United States Patent
Mitkidis (10) Patent No.: US 11,117,848 B2
(45) Date of Patent: Sep. 14, 2021

(54) OXIDATIVE COUPLING OF METHANE

(71) Applicant: SHELL OIL COMPANY, Houston, TX (US)

(72) Inventor: Georgios Mitkidis, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 76 days.

(21) Appl. No.: 16/500,249

(22) PCT Filed: Apr. 9, 2018

(86) PCT No.: PCT/EP2018/059008
§ 371 (c)(1),
(2) Date: Oct. 2, 2019

(87) PCT Pub. No.: WO2018/189097
PCT Pub. Date: Oct. 18, 2018

(65) Prior Publication Data
US 2021/0130259 A1   May 6, 2021

(30) Foreign Application Priority Data
Apr. 10, 2017 (EP) .................................. 17386015

(51) Int. Cl.
*C07C 2/84* (2006.01)
*B01D 53/14* (2006.01)
(Continued)

(52) U.S. Cl.
CPC .............. *C07C 2/84* (2013.01); *B01D 3/145* (2013.01); *B01D 53/047* (2013.01);
(Continued)

(58) Field of Classification Search
None
See application file for complete search history.

(56) References Cited

U.S. PATENT DOCUMENTS 3,758,605 A * 9/1973 Hughes .................. C07C 11/04
585/818
4,443,649 A    4/1984 Jones et al.
(Continued)

FOREIGN PATENT DOCUMENTS

CA    2016675 A1    11/1991
CA    2918287 A1    1/2015
(Continued)

OTHER PUBLICATIONS

International Search Report and Written Opinion received for PCT Patent Application No. PCT/EP2018/059008, dated Jun. 6, 2018, 11 pages.
(Continued)

*Primary Examiner* — Philip Y Louie
(74) *Attorney, Agent, or Firm* — Shell Oil Company (57) ABSTRACT

The present invention relates to a process for oxidative coupling of methane (OCM), comprising the steps of: (a) contacting, in a reactor, oxygen and methane with an OCM catalyst, resulting in a reactor effluent comprising ethylene, ethane, methane, carbon dioxide and water; (b) cooling the reactor effluent to obtain a liquid stream comprising water and a gas stream comprising ethylene, ethane, methane and carbon dioxide; (c) removing carbon dioxide from at least a part of the gas stream comprising ethylene, ethane, methane and carbon dioxide resulting in a gas stream comprising ethylene, ethane and methane; (d) passing at least a part of the gas stream comprising ethylene, ethane and methane as obtained in step (c) through a membrane, preferably a membrane comprising metal cations, more preferably a membrane comprising silver (I) ions ($Ag^+$ ions) or copper (I) ions ($Cu^+$ ions), to obtain a stream comprising ethane and a stream comprising ethylene.

13 Claims, 3 Drawing Sheets

| (51) | Int. Cl. | |
|---|---|---|
| | B01D 53/22 | (2006.01) |
| | B01D 3/14 | (2006.01) |
| | B01D 53/047 | (2006.01) |
| | C07C 7/00 | (2006.01) |
| | C07C 7/04 | (2006.01) |
| | C07C 7/12 | (2006.01) |
| | C07C 7/144 | (2006.01) |

(52) U.S. Cl.
CPC ..... *B01D 53/1431* (2013.01); *B01D 53/1475* (2013.01); *B01D 53/225* (2013.01); *B01D 53/228* (2013.01); *B01D 53/229* (2013.01); *C07C 7/005* (2013.01); *C07C 7/04* (2013.01); *C07C 7/12* (2013.01); *C07C 7/144* (2013.01); *B01D 2252/10* (2013.01); *B01D 2252/204* (2013.01); *B01D 2256/24* (2013.01); *B01D 2257/7025* (2013.01)

(56) References Cited

U.S. PATENT DOCUMENTS

| | | |
|---|---|---|
| 4,769,508 A | 9/1988 | Gastinger et al. |
| 5,025,108 A | 6/1991 | Cameron et al. |
| 5,113,032 A | 5/1992 | Cameron et al. |
| 6,596,912 B1 | 7/2003 | Lunsford et al. |
| 2013/0023709 A1 | 1/2013 | Cizeron et al. |
| 2013/0178680 A1 | 7/2013 | Ha et al. |
| 2014/0080699 A1 | 3/2014 | Ghose et al. |
| 2014/0249339 A1 | 9/2014 | Simanzhenkov et al. |
| 2017/0137355 A1* | 5/2017 | Sarsani ............... C07C 2/82 |
| 2017/0297975 A1* | 10/2017 | Radaelli ............... C07C 2/84 |
| 2018/0169561 A1* | 6/2018 | Jonnavittula ........ B01J 20/3491 |
| 2019/0169090 A1* | 6/2019 | Sarsani ............... C07C 2/84 |

FOREIGN PATENT DOCUMENTS

| | | |
|---|---|---|
| EP | 0206042 A1 | 12/1986 |
| WO | 2004096415 A1 | 11/2004 |
| WO | 2008134484 A2 | 11/2008 |
| WO | 2010080753 A1 | 7/2010 |
| WO | 2010133461 A1 | 11/2010 |
| WO | 2012167362 A1 | 12/2012 |
| WO | 2013106771 A2 | 7/2013 |
| WO | 2014089479 A1 | 6/2014 |
| WO | 2015105911 A1 | 7/2015 |
| WO | 2016200504 A1 | 12/2016 |

OTHER PUBLICATIONS

Hall et al., "Effects of Product Separation of the Kinetics and Selectivity of Oxidative Coupling", Methane and Alkane Conversion Chemistry, Jan. 1995, pp. 123-130, XP008042019.

Cordi et al. "Steady-State Production of Olefins in High Yields During the Oxidative Coupling of Methane Utilization of a Membrane Contactor" Applied Catalysis A: General, vol. 155, Issue No. 1, Jul. 1997, pp. LI-L7, XP055402009.

Chua et al., "Oxidative Coupling of Methane for the Production of Ethylene over-Sodium-Tungsten-Manganese-Supported-Silica Catalyst(Na—W—Mn/SiO2)", Applied Catalysis A: General, vol. 343, 2008, pp. 142-148.

Arndt et al., "Mn—na2wo4/sio2 as Catalyst for the Oxidative Coupling of Methane. What is Really Known?", Applied Catalysis A: General, vol. 425-426, 2012, pp. 53-61.

Lee et al., "Scaled-up Production of C2 Hydrocarbons by the Oxidative Coupling of Methane Over Pelletized Na2wo4/Mn/sio2 Catalysts: Observing Hot Spots for the Selective Process", Fuel, vol. 106, 2013, pp. 851-857.

Gong et al., "Study on the Oxidative Coupling of Methane: XRD and XPS Study of TiO2-based Catalysts Promoted by Different Additives", Catalysis Today, vol. 24, 1995, pp. 259-261.

Jeon et al., "Oxidative Coupling of Methane to C2 Hydrocarbons on the MG-TI Mixed Oxide-supported Catalysts at the Lower Reaction Temperature: Role of Surface Oxygen Atoms", Applied Catalysis A: General, vol. 464-465, 2013, pp. 68-77.

Gong et al., "Study on Oxidative Coupling of Methane. Effect of Additives on TiO2-based Catalytic Performance", Catalysis Today, vol. 24, 1995, pp. 263-264.

* cited by examiner

OXIDATIVE COUPLING OF METHANE

CROSS REFERENCE TO RELATED APPLICATIONS

This is a national stage application of International Application No. PCT/EP2018/059008, filed 9 Apr 2018, which claims benefit of priority to European Patent Application No. 17386015.6, filed 10 Apr. 2017.

FIELD OF THE INVENTION

The present invention relates to a process for oxidative coupling of methane (OCM).

BACKGROUND OF THE INVENTION

Methane is a valuable resource which is used not only as a fuel, but is also used in the synthesis of chemical compounds such as higher hydrocarbons.

The conversion of methane to other chemical compounds can take place via indirect conversion wherein methane is reformed to synthesis gas (hydrogen and carbon monoxide), followed by reaction of the synthesis gas in a Fischer-Tropsch process. However, such indirect conversion is costly and consumes a lot of energy.

Consequently, it is desirable for industry to be able to convert methane directly to other chemical compounds without requiring the formation of intermediates such as synthesis gas. To this end, there has been increasing focus in recent years on the development of processes for the oxidative coupling of methane (OCM).

The oxidative coupling of methane converts methane into saturated and unsaturated, non-aromatic hydrocarbons having 2 or more carbon atoms, including ethylene. In this process, a gas stream comprising methane is contacted with an OCM catalyst and with an oxidant, such as oxygen. In such a process, the oxygen is adsorbed on the catalyst's surface. Methane molecules are then converted into methyl radicals. Two methyl radicals are first coupled into one ethane molecule, which is then dehydrogenated into ethylene via an ethyl radical intermediate.

In general, the conversion that can be achieved in an OCM process is relatively low. Besides, at a higher conversion, the selectivity decreases so that it is generally desired to keep the conversion low. As a result, a relatively large amount of unconverted methane leaves the OCM reactor. The proportion of unconverted methane in the OCM product gas stream may be as high as 60 to 80 mole % based on the total molar amount of the gas stream. This unconverted methane has to be recovered from the desired products, such as ethylene and other saturated and unsaturated hydrocarbons having 2 or more carbon atoms, which are also present in such gas streams.

It is known to separate the gas stream leaving an OCM process in the following way. Acid gas (mainly $CO_2$) is removed in two stages, the first stage is an aqueous amine absorption system, using for example monoethanolamine (MEA), and the second stage removes final traces of $CO_2$ by scrubbing against aqueous NaOH. The $CO_2$-free gas is dried in a dessicant bed and processed in a separation train similar to that used in conventional ethylene plants. The separation sequence comprises a front end demethanizer, deethanizer, C2 splitter, depropanizer, C3 splitter, and a debutanizer. The cryogenic needs for separation are met by a propylene-ethylene cascade refrigeration system that requires ethylene refrigerant only for the demethanization stage.

Thus, it is known to separate methane from saturated and unsaturated hydrocarbons having 2 or more carbon atoms, such as ethylene, by means of cryogenic distillation in so-called "demethanizer" columns. In cryogenic distillation, a relatively high pressure and a relatively low (cryogenic) temperature are applied to effect the separation of methane. The use of cryogenic distillation following an OCM process is for example disclosed in U.S. Pat. Nos. 5,113,032 and 5,025,108.

It is an objective of the present invention to provide an improved process for oxidative coupling of methane. One aim is to obtain relatively pure ethylene. Another aim is to reduce the energy required for purifying ethylene.

SUMMARY OF THE INVENTION

Surprisingly it was found that the above-mentioned objectives may be obtained by means of the OCM process of the present invention.

The present invention relates to a process for oxidative coupling of methane (OCM), comprising the steps of:
(a) contacting, in a reactor, oxygen and methane with an OCM catalyst, resulting in a reactor effluent comprising ethylene, ethane, methane, carbon dioxide and water;
(b) cooling the reactor effluent to obtain a liquid stream comprising water and a gas stream comprising ethylene, ethane, methane and carbon dioxide;
(c) removing carbon dioxide from at least a part of the gas stream comprising ethylene, ethane, methane and carbon dioxide resulting in a gas stream comprising ethylene, ethane and methane;
(d) passing at least a part of the gas stream comprising ethylene, ethane and methane as obtained in step (c) through a membrane, preferably a membrane comprising metal cations, more preferably a membrane comprising silver(I) ions ($Ag^+$ ions) or copper(I) ions ($Cu^+$ ions), to obtain a stream comprising ethane and a stream comprising ethylene.

In the process of the present invention additional steps may be present. For example, use may be made of one or more additional membranes. Additionally or alternatively, a distillation step may be added. Additionally or alternatively, use may be made of a Pressure Swing Adsorption (PSA) unit.

With the OCM process of the present invention, especially with the preferred embodiments that will be discussed below, it is possible to obtain a high yield of relative pure ethylene at a reduced energy demand.

DETAILED DESCRIPTION OF THE INVENTION

Figure 1:
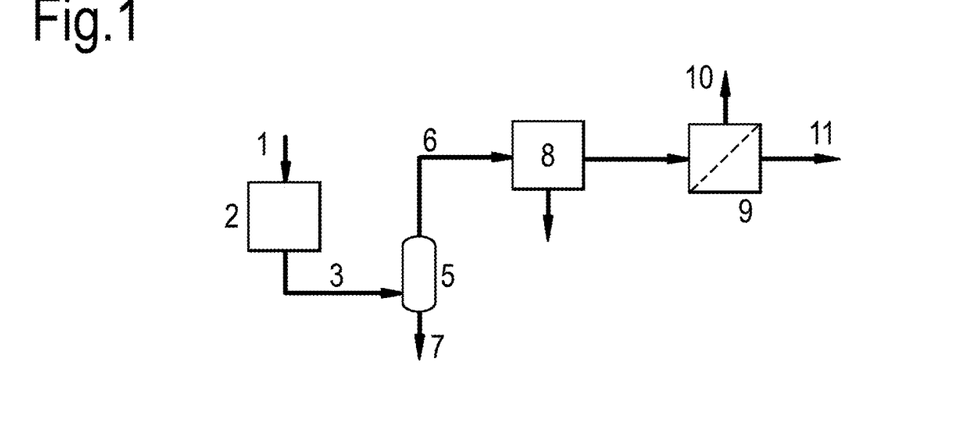
FIG. 1 is a schematic drawing of a process for oxidative coupling of methane in accordance with one embodiment of the present invention.

The present invention relates to a process for oxidative coupling of methane according to claim 1. A schematic drawing of a process for oxidative coupling of methane in accordance with one embodiment of the present invention is shown in FIG. 1, which is described in detail in the "Figures" section.

Step (a)

In step (a) oxygen and methane are contacted with a catalyst in a reactor, preferably an OCM reactor.

In step (a), an OCM reactor may be any reactor suitable for the oxidative coupling of methane, such as a fixed bed reactor with axial or radial flow and with inter-stage cooling or a fluidized bed reactor equipped with internal and external heat exchangers.

In one embodiment of the present invention, a catalyst composition comprising a methane oxidative coupling (OCM) catalyst may be packed along with an inert packing material, such as quartz, into a fixed bed reactor having an appropriate inner diameter and length.

Optionally, such catalyst composition may be pretreated at high temperature to remove moisture and impurities therefrom. Said pretreatment may take place, for example, at a temperature in the range of from 100-300° C. for about one hour in the presence of an inert gas such as helium.

Various processes and reactor set-ups are described in the OCM field and the process of the present invention is not limited in that regard. The person skilled in the art may conveniently employ any of such processes in the reaction step of the process of the present invention.

Suitable processes include those described in EP0206042A1, U.S. Pat. No. 4,443,649, CA2016675, U.S. Pat. No. 6,596,912, US20130023709, WO2008134484 and WO2013106771.

As used herein, the term "reactor feed" is understood to refer to the totality of the gas stream(s) at the inlet(s) of the reactor. Thus, as will be appreciated by one skilled in the art, the reactor feed is often comprised of a combination of one or more gas stream(s), such as a methane stream, an oxygen stream, an air stream, a recycle gas stream, etc. For example, in one embodiment, a gas stream comprising methane and another gas stream comprising oxygen are fed to the reactor. In another embodiment, a gas stream comprising methane and oxygen is fed to the reactor.

The one gas stream or multiple gas streams which may be fed to the OCM reactor may additionally comprise an inert gas. An inert gas is defined as a gas that does not take part in the oxidative coupling of methane. The inert gas may be selected from the group consisting of the noble gases and nitrogen ($N_2$). Preferably, the inert gas is nitrogen or argon, more preferably nitrogen. In case air is fed to the reactor, one or multiple gas streams comprise oxygen as well as nitrogen.

During the oxidative coupling of methane in reaction step (a), a reactor feed comprising methane and oxygen may be introduced into the reactor, so that methane and oxygen are contacted with a methane oxidative coupling catalyst inside that reactor.

A gas stream comprising oxygen (to be combined with the methane in reaction step (a)) may be a high purity oxygen stream. Such high-purity oxygen may have a purity greater than 90%, preferably greater than 95%, more preferably greater than 99%, and most preferably greater than 99.4%.

In reaction step (a) of the process of the present invention, methane and oxygen may be added to the reactor as mixed feed, optionally comprising further components therein, at the same reactor inlet. Alternatively, the methane and oxygen may be added in separate feeds, optionally comprising further components therein, to the reactor at the same reactor inlet or at separate reactor inlets.

In reaction step (a) of the process of the present invention, the methane:oxygen molar ratio in a reactor feed may be in the range of from 2:1 to 10:1, more preferably 3:1 to 6:1. In a case wherein in the present invention air is used as the oxidant in reaction step (a), such methane:oxygen molar ratios correspond to methane:air molar ratios of 2:4.8 to 10:4.8 and 3:4.8 to 6:4.8, respectively.

Methane may be present in a reactor feed in a concentration of at least 35 mole %, more preferably at least 40 mole %, relative to the reactor feed. Further, methane may be present in a reactor feed in a concentration of at most 90 mole %, more preferably at most 85 mole %, most preferably at most 80 mole %, relative to the reactor feed. Thus, in the present invention, methane may for example be present in a reactor feed in a concentration in the range of from 35 to 90 mole %, more preferably 40 to 85 mole %, most preferably 40 to 80 mole %, relative to the reactor feed. In the context of the present invention, the components of said reactor feed are to be selected in an overall amount not to exceed 100 vol. %.

In general, the oxygen concentration in a reactor feed should be less than the concentration of oxygen that would form a flammable mixture at either the reactor inlet or the reactor outlet at the prevailing operating conditions.

The ratio of the methane to oxygen and volume percentages for the various components in a reactor feed are the ratio and volume percentages, respectively, at the entrance of the catalyst bed. Obviously, after entering the catalyst bed, at least part of the oxygen and methane from the gas stream gets consumed.

In reaction step (a), a reactor feed comprising methane and oxygen may be contacted with a methane oxidative coupling (OCM) catalyst so that methane is converted to one or more C2+ hydrocarbons, including ethylene. Suitably, the reactor temperature in said reaction step is in the range of from 500 to 1000° C. Preferably, said conversion is effected at a reactor temperature in the range of from 700 to 1100° C., more preferably 700 to 1000° C., even more preferably 750 to 950° C.

In a preferred embodiment, said conversion of methane to one or more C2+ hydrocarbons is effected at a reactor pressure in the range of from 0.1 to 20 bar, more preferably 0.5 to 20 bar, more preferably 1 to 15 bar, more preferably 2 to 10 bar.

According to the present invention, the above-mentioned methane oxidative coupling catalyst may be any methane oxidative coupling catalyst. Generally, the catalyst may contain one or more of manganese, one or more alkali metals (e.g. sodium) and tungsten. Preferably, the catalyst contains manganese, one or more alkali metals (e.g. sodium) and tungsten. Said carrier may be unsupported or supported. In particular, the catalyst may be a mixed metal oxide catalyst containing manganese, one or more alkali metals (e.g. sodium) and tungsten. Further, the catalyst may be a supported catalyst, such as a catalyst comprising manganese, one or more alkali metals (e.g. sodium) and tungsten on a carrier. The carrier may be any carrier, such as silica or a metal-containing carrier. A particular suitable catalyst comprises manganese, tungsten and sodium on a silica carrier (Mn—$Na_2WO_4$/$SiO_2$).

Suitable methane oxidative coupling catalysts are described in the following publications.

Chua et al. studied the oxidative coupling of methane for the production of ethylene over sodium-tungsten-manganese-supported silica catalyst (Na—W—Mn/$SiO_2$) in Applied Catalysis A: General 343 (2008) 142-148.

The performance of Mn—$Na_2WO_4$/$SiO_2$ catalyst was further reviewed by Arndt et al. in Applied Catalysis A: General 425-426 (2012) 53-61 and Lee et al. in Fuel 106 (2013) 851-857.

US20130023709 describes the high throughput screening of catalyst libraries for the oxidative coupling of methane and tests various catalysts including catalysts comprising sodium, manganese and tungsten on silica and zirconia carriers.

US20140080699 describes a specific method for the preparation of catalysts such as Mn—$Na_2WO_4$/$SiO_2$ catalyst which is said to provide an improved catalyst material.

Various manganese and titanium-containing catalysts for the oxidative coupling of methane are researched in the literature and are disclosed in various patent publications including Gong et al. Catalysis Today 24 (1995), 259-261, Gong et al. Catalysis Today 24 (1995), 263-264, Jeon et al. Applied Catalysis A: General 464-465 (2013) 68-77, U.S. Pat. No. 4,769,508 and US20130178680.

The amount of the catalyst in said process is not essential. Preferably, a catalytically effective amount of the catalyst is used, that is to say an amount sufficient to promote a methane oxidative coupling reaction in step (a).

In step (a) of the process of the present invention, the gas hourly space velocity (GHSV; in $m^3$ gas/$m^3$ catalyst/hr) may typically be of from 100 to 50,000 $hr^{-1}$. Said GHSV is measured at standard temperature and pressure, namely 32° F. (0° C.) and 1 bara (100 kPa). In a preferred embodiment of the present invention, said GHSV is of from 2,500 to 25,000 $hr^{-1}$, more preferably of from 5,000 to 20,000 $hr^{-1}$, most preferably of from 7,500 to 15,000 $hr^{-1}$.

The catalyst used in step (a) may be a particulate catalyst, preferably a heterogeneous catalyst in the form of particles. The particles may be of any size suitable to be used in the reactor. The particles may be small enough to be used in a fluidized bed reactor. Alternatively, the particles may be arranged in a catalyst bed in the reactor. In that case the reactor may be a (multi-) tubular fixed bed reactor. Such a catalyst bed may comprise pellets, extrudates, or catalyst on a metal support (like a metal wire or metal flake). In addition to catalyst particles, the catalyst bed may also contain inert particles, i.e. catalytically inactive particles.

During step (a), ethane, ethylene and water are formed by oxidative coupling of methane. Further, carbon dioxide is formed as a by-product. During step (a) gas is fed to the reactor and an effluent is withdrawn from the reactor. The reactor effluent comprises ethylene, ethane, methane, carbon dioxide and water. Said methane comprises unconverted methane.

Step (b)

In step (b) the reactor effluent is cooled, for example from the reaction temperature to a lower temperature, for example room temperature, so that the water condenses and can then be removed from the gas stream (reactor effluent).

In step (b), by cooling the reactor effluent, a liquid stream comprising water and a gas stream comprising ethylene, ethane, methane and carbon dioxide are obtained.

Step (c)

In step (c) carbon dioxide is removed from at least a part of the gas stream comprising ethylene, ethane, methane and carbon dioxide, resulting in a gas stream comprising ethylene, methane and ethane. This is preferably performed using one or more amines and/or by means of caustic treating. Caustic treating may be performed, for example, using a sodium hydroxide solution. A suitable carbon dioxide removal agent may be an aqueous solution of a base, for example sodium hydroxide or an amine.

Step (d)

In step (d) at least a part of the gas stream comprising ethylene, ethane and methane as obtained in step (c) is passed through a membrane. A stream comprising ethane and a stream comprising ethylene are obtained in step (d). In case the stream that is subjected to step (d) comprises ethylene, ethane and methane, step (d) results in a stream comprising ethane and methane and a stream comprising ethylene.

As further described below, before carrying out step (d), the gas stream comprising ethylene, ethane and methane as obtained in step (c) may be separated into a stream comprising methane and a stream comprising ethylene, ethane and optionally methane. The latter stream comprising ethylene, ethane and optionally methane is subjected to step (d), resulting in a stream comprising ethane and optionally methane and a stream comprising ethylene. By separating the gas stream comprising ethylene, ethane and methane as obtained in step (c) into a stream comprising methane and a stream comprising ethylene, ethane and optionally methane, the ethylene concentration, and thus the ethylene partial pressure, in the stream comprising ethylene, ethane and optionally methane is increased. When this stream, having an increased ethylene partial pressure compared to the gas stream comprising ethylene, ethane and methane as obtained in step (c), is subsequently subjected to step (d), the increased ethylene partial pressure may require a lower membrane surface to separate the ethylene compared to separating the ethylene from the stream comprising ethylene, ethane and methane.

Further, the gas stream that is subjected to step (d) may comprise nitrogen. For example, said nitrogen may originate from air fed as oxygen containing source to step (a). As described above, the stream comprising ethane as obtained in step (d) may comprise methane. Further, the stream comprising ethane as obtained in step (d) optionally comprises nitrogen.

Optionally, at least a part of the stream comprising ethane as obtained in step (d) may be fed to step (a). For example, at least a part of a stream comprising ethane and methane as obtained in step (d) may be fed to step (a).

Further, optionally, at least a part of a stream comprising ethane and methane as obtained in step (d) may be separated into a stream comprising ethane and a stream comprising methane. The latter separated stream comprising methane may be fed to step (a). The latter separated stream comprising ethane may be converted to ethylene, for example by subjecting it to ethane cracking (pyrolysis) conditions.

Figure 6:
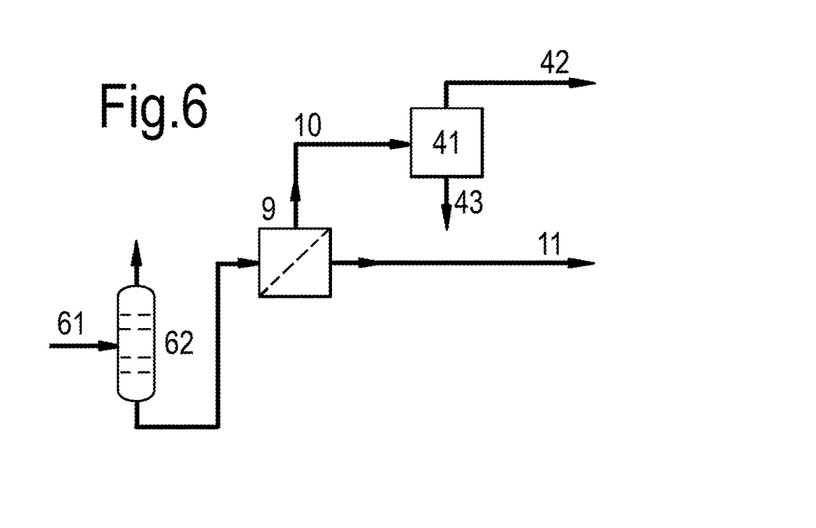
FIG. 6 is a schematic drawing of a part of a preferred process in which a distillation column, a membrane and a PSA unit are used.

At least a part of the gas stream comprising ethylene, ethane and methane as obtained in step (c) may be subjected to distillation, to remove methane, before it is passed through the membrane in step (d). Preferably, before carrying out said distillation, any water is removed. Said water may be residual water originating from the carbon dioxide removal agent used in step (c). Said water may for example be removed by means of molecular sieves or glycol dehydration. Said distillation step results in a top stream comprising methane and a bottom stream comprising ethylene, ethane and optionally methane. Said bottom stream is sent to step (d). Said distillation step before step (d) is illustrated in FIG. 6, as further described below.

Figure 7:
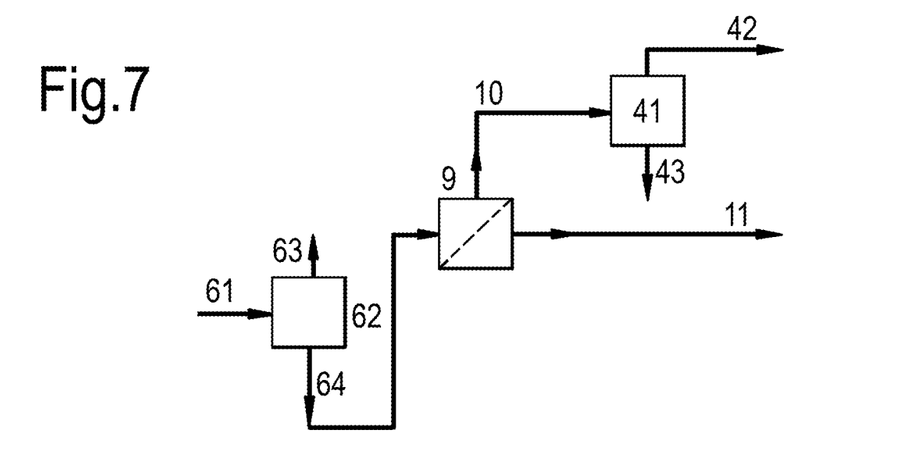
FIG. 7 is a schematic drawing of a part of a preferred process in which a PSA unit, a membrane and another PSA unit are used.
Figure 8:
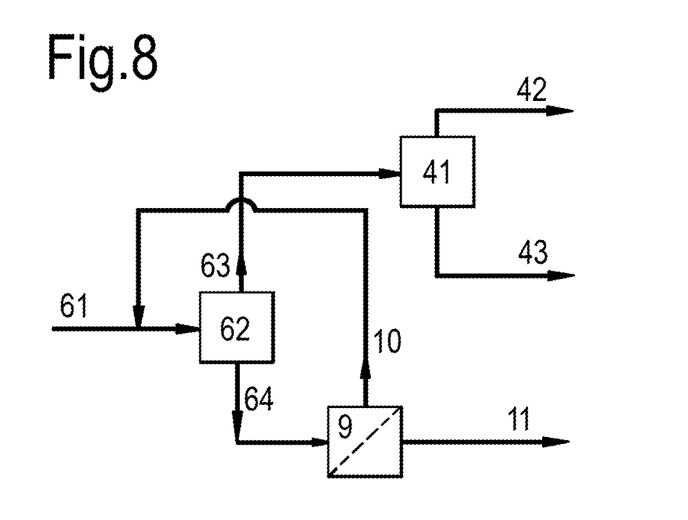
FIG. 8 is a schematic drawing of a part of a preferred process in which two PSA units and a membrane are used, in addition to a recycle.

Alternatively, at least a part of the gas stream comprising ethylene, ethane and methane as obtained in step (c) may be fed to a Pressure Swing Adsorption (PSA) unit, to remove methane, before it is passed through the membrane in step (d). Optionally, before carrying out said PSA step, any water is removed, as described above. Said PSA step results in a stream comprising methane and a stream comprising ethylene, ethane and optionally methane. The latter stream is sent to step (d). Said PSA step before step (d) is illustrated in FIGS. 7 and 8, as further described below.

PSA units are commercially available. Suitable adsorbents to be used in the PSA unit are, for example, molecular sieves, zeolites, such as zeolite 13X and zeolite 5A, activated carbon, silica gel, activated alumina and crystalline titanium silicate. In the PSA unit, the pressure in a desorption step is lower than the pressure in the sorption step that directly precedes said desorption step. In case desorption is effected by reducing the pressure, the pressure in said sorption step may be the same as the pressure at which the preceding step is operated. The temperature in the PSA unit may vary within wide ranges. Preferably, the temperature is in the range of from 0 to 200° C., more preferably 25 to 175° C., most preferably 50 to 150° C. Advantageously, said step may be carried out at a non-cryogenic temperature, e.g. of from 0 to 110° C.

Preferably the membrane used in step (d) comprises metal cations, more preferably transition metal cations. Any membrane comprising metal cations, capable of separating ethylene from ethane, may be used. Ethylene may preferentially complex to said metal cations. For example, the membrane may comprise one or more metal cations selected from the group consisting of silver(I) ions ($Ag^+$ ions), copper(I) ions ($Cu^+$ ions), gold(I) ions ($Au^+$ ions), nickel(II) ions ($Ni^{2+}$ ions), platinum(II) ions ($Pt^{2+}$ ions), palladium(II) ions ($Pd^{2+}$ ions). Suitably, the membrane comprises silver(I) ions or copper(I) ions, more suitably silver(I) ions.

Suitable membranes which may be used in step (d) are for example available from Imtex (Innovative Membrane Technologies) and CMS (Compact Membrane Systems). Suitable membranes which may be used in step (d) are membranes as described in WO2004096415, WO2012167362, WO201080753 and CA2918287, the disclosures of which are herein incorporated by reference.

Suitable membranes which may be used in step (d) comprise a supporting substrate and additionally a layer comprising the above-mentioned metal cations. Any supporting substrate may be used. For example, the supporting substrate may comprise a polyester, polyamide, polyimide, polyacrylonitrile, polysulphone, polycarbonate, or a combination thereof. Further, said layer comprising the above-mentioned metal cations may be composed of any material. For example, said cations containing layer may be a polysaccharide layer, in particular a chitosan layer.

A further suitable membrane which may be used in step (d) comprises a nonporous, selectively permeable layer of a copolymer comprising copolymerized perfluorinated cyclic or cyclizable monomer, and a 4-carbon acid/anhydride, wherein the copolymer may further comprise an acyclic fluorinated olefinic monomer. In particular, a metal exchanged fluorinated ionomer may be used which is a copolymer minimally including repeating units of (i) a polymerized derivative of a perfluorinated cyclic or cyclizable monomer and (ii) a strong acid highly fluorinated vinylether compound in which the acid moiety is exchanged with a cation of a Group 11 metal. Metal exchanged fluorinated ionomers are readily soluble and can be formed into thin, selectively gas permeable membranes by solution deposition methods.

The membrane used in step (d) preferably is operated at a pressure in the range of from 1 to 100 bara, preferably 2 to 50 bara, more preferably 5 to 25 bara. The membrane used in step (d) preferably is operated at a temperature in the range of from 0 to 150° C., preferably 10 to 100° C., more preferably 20 to 60° C.

In a case wherein in one of the below-described optional further steps, separation using a further membrane ("second membrane") is carried out, such further membrane separation step may be carried out in the same way as step (d), using a "first membrane", as described above.

Further, in a case wherein in one of the below-described optional further steps, separation using Pressure Swing Adsorption (PSA) is carried out, such further PSA separation step may be carried out in the same way as the above-described optional PSA step before step (d).

As mentioned above, it is an objective of the present invention to provide an improved process for oxidative coupling of methane. One aim is to obtain relatively pure ethylene. Another aim is to reduce the energy required for purifying ethylene. The above-mentioned objectives may be obtained by means of the OCM process of the present invention including membrane separation step (d), due to one or more of the following: 1) removal of light columns and de-methanizer; 2) removal of (methane/ethylene) coldbox; 3) removal of C2 and C3 splitters; 4) flexibility to use air as oxidant causing optional removal of air separation unit. In the present invention, a relatively high recovery of ethylene may be obtained.

Optional Further Steps

The process of the present invention may comprise one of the following further steps.

In a case wherein the stream comprising ethane as obtained in step (d) also comprises methane, one of the following further steps may be performed.

Figure 2:
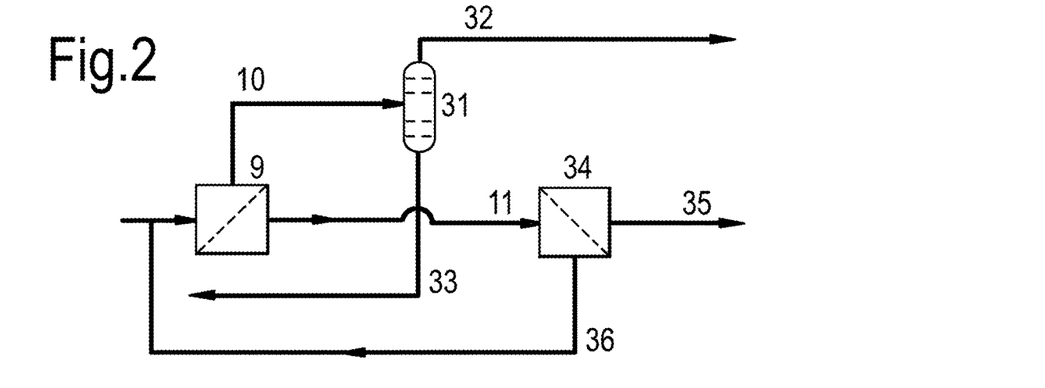
FIG. 2 is a schematic drawing of a part of a preferred process in which two membranes and a distillation column are used.

At least part of a stream comprising ethane and methane as obtained in step (d) may be subjected to distillation, resulting in a top stream comprising methane and a bottom stream comprising ethane. Preferably, before carrying out said distillation, any water is removed, as described above. At least part of the stream comprising methane as obtained in this distillation step may be fed to step (a). At least part of the stream comprising ethane as obtained in this distillation step may be converted to ethylene, for example by subjecting it to ethane cracking (pyrolysis) conditions as described above. Said distillation step after step (d) is illustrated in FIG. 2, as further described below.

Further, at least part of a stream comprising ethane and methane as obtained in step (d) may be fed to a Pressure Swing Adsorption (PSA) unit to obtain a stream comprising ethane and a stream comprising methane. At least part of the stream comprising methane as obtained in this PSA step may be fed to step (a). At least part of the stream comprising ethane as obtained in this PSA step may be converted to ethylene, for example by subjecting it to ethane cracking (pyrolysis) conditions as described above. Said PSA step after step (d) is illustrated in FIGS. 3, 4, 5, 6 and 7, as further described below.

Further, in a case wherein the stream comprising ethylene as obtained in step (d) also comprises ethane, one of the following further steps may be performed.

Figure 5:
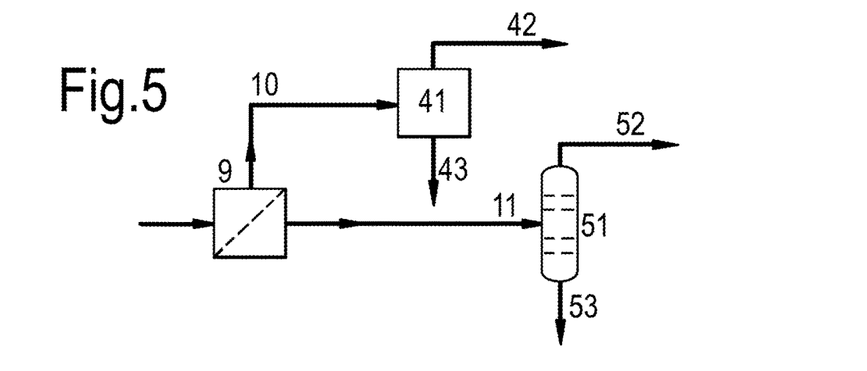
FIG. 5 is a schematic drawing of a part of a preferred process in which one membrane, a PSA unit, and a distillation column are used.

At least part of a stream comprising ethane and ethylene as obtained in step (d) may be subjected to distillation, resulting in a top stream comprising ethylene and a bottom stream comprising ethane. The former stream comprising ethylene may be a stream of high purity ethylene of polymer grade. Preferably, before carrying out said distillation, any water is removed, as described above. At least part of the stream comprising ethane as obtained in this distillation step may be fed to step (a). Alternatively, at least part of the stream comprising ethane as obtained in this distillation step may be converted to ethylene, for example by subjecting it to ethane cracking (pyrolysis) conditions as described above. Said distillation step after step (d) is illustrated in FIG. 5, as further described below.

Figure 4:
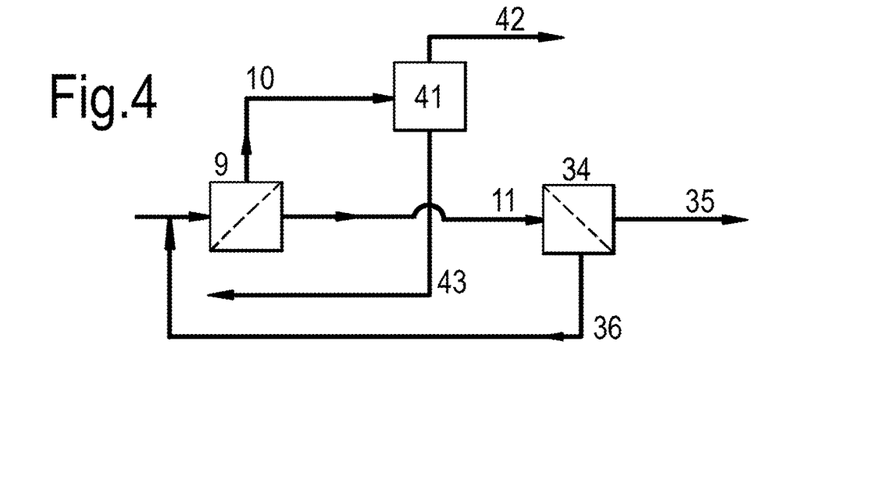
FIG. 4 is a schematic drawing of a part of a preferred embodiment in which two membranes and a PSA unit are used.

Further, at least part of a stream comprising ethane and ethylene as obtained in step (d) may be passed through a second membrane, preferably a membrane comprising metal cations, more preferably a membrane comprising silver(I) ions ($Ag^+$ ions) or copper(I) ions ($Cu^+$ ions), to obtain a stream comprising ethane and a stream comprising ethylene. The latter stream comprising ethylene may be a stream of high purity ethylene of polymer grade. At least part of the stream comprising ethane as obtained in this second membrane separation step may be fed to step (a). Alternatively, at least part of the stream comprising ethane as obtained in this second membrane separation step may be converted to ethylene, for example by subjecting it to ethane cracking (pyrolysis) conditions as described above. Said second membrane separation step after step (d) is illustrated in FIGS. 2 and 4, as further described below.

Further, more specific embodiments of the present invention are described hereinbelow.

Two Membranes and a Distillation

In one preferred embodiment of the process use is made of two membranes and a distillation column. A schematic drawing of a preferred example of this embodiment is shown in FIG. 2, which is described in detail in the "Figures" section. One stream obtained by means of the first membrane is fed to a distillation column. Another stream obtained by means of the first membrane is fed to a second membrane.

In this preferred embodiment, in step (d) a stream comprising ethane and methane and a stream comprising ethylene and ethane are obtained, and step (d) is followed by the following steps:
  (e) feeding the stream comprising ethane and methane as obtained in step (d) to a distillation column to obtain a stream comprising ethane and a stream comprising methane;
  (f) optionally feeding at least a part of the stream comprising methane as obtained in step (e) to step (a);
  (g) passing at least a part of the stream comprising ethylene and ethane as obtained in step (d) through a second membrane, preferably a membrane comprising metal cations, more preferably a membrane comprising comprising silver(I) ions ($Ag^+$ ions) or copper(I) ions ($Cu^+$ ions), to obtain a stream comprising ethane and ethylene and a stream comprising ethylene;
  (h) optionally feeding at least a part of the stream comprising ethane and ethylene as obtained in step (g) to the membrane used in step (d), that is to say to the first membrane, or optionally feeding at least a part of the stream comprising ethane and ethylene as obtained in step (g) to step (a).

The distillation in step (e) preferably is performed at a pressure in the range of from 1 to 100 bara, preferably 10 to 50 bara, more preferably 15 to 35 bara. At least a part of the stream comprising ethane as obtained in the distillation step may be fed to step (a). Alternatively or additionally, at least a part of the stream comprising ethane as obtained in the distillation step may be converted to ethylene, for example by subjecting it to ethane cracking (pyrolysis) conditions.

Step (f) is optional. In step (f) at least a part of the stream comprising methane as obtained in step (e) is fed to the reactor, the OCM reactor, used in step (a). This stream can be fed directly to the reactor, or it can be mixed with a stream comprising oxygen and/or a stream comprising methane before it is fed to the reactor.

In step (g) at least a part of the stream comprising ethylene and ethane as obtained in step (d) is passed through a second membrane. Step (g) may be carried out in the same way as step (d) as described above. In particular, the second membrane used in step (g) may be the same or different as compared to the first membrane which is used in step (d).

Step (h) is optional. Step (h) is a recycle step. Alternatively or additionally, in said step (h), at least a part of the stream comprising ethane and ethylene as obtained in step (g) may be converted to ethylene, for example by subjecting it to ethane cracking (pyrolysis) conditions.

One Membrane and a PSA Unit

Figure 3:
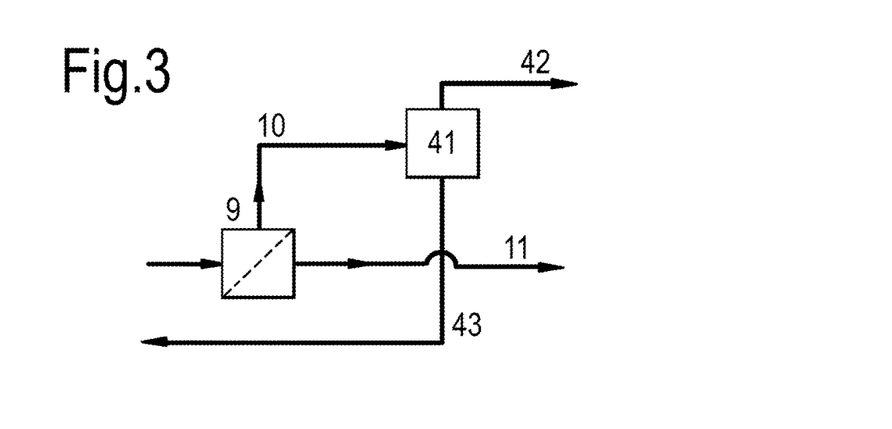
FIG. 3 is a schematic drawing of a part of a preferred process in which one membrane and a PSA unit are used.

In one preferred embodiment of the process use is made of one membrane and a Pressure Swing Adsorption (PSA) unit. A schematic drawing of a preferred example of this embodiment is shown in FIG. 3, which is described in detail in the "Figures" section. One stream obtained by means of the membrane is fed to a PSA unit.

In this preferred embodiment, the stream comprising ethane as obtained in step (d) additionally comprises methane, and step (d) is followed by the following steps:
  (eA) feeding the stream comprising ethane and methane as obtained in step (d) to a Pressure Swing Adsorption (PSA) unit to obtain a stream comprising ethane and a stream comprising methane;
  (fA) optionally feeding at least a part of the stream comprising methane as obtained in step (eA) to step (a).

Step (eA), using a Pressure Swing Adsorption (PSA) unit, may be carried out in the same way as the PSA step as described above. At least a part of the stream comprising ethane as obtained in step (eA) may be fed to step (a). Alternatively or additionally, at least a part of the stream comprising ethane as obtained in step (eA) may be converted to ethylene, for example by subjecting it to ethane cracking (pyrolysis) conditions.

Two Membranes and a PSA Unit

In one preferred embodiment of the process use is made of two membranes and a Pressure Swing Adsorption (PSA) unit. A schematic drawing of a preferred example of this embodiment is shown in FIG. 4, which is described in detail in the "Figures" section.

In this preferred embodiment, in step (d) a stream comprising ethane and methane and a stream comprising ethylene and ethane are obtained, and step (d) is followed by the following steps:
  (eA) feeding the stream comprising ethane and methane as obtained in step (d) to a Pressure Swing Adsorption (PSA) unit to obtain a stream comprising ethane and a stream comprising methane;

(fA) optionally feeding at least a part of the stream comprising methane as obtained in step (eA) to step (a);

(gA) passing at least a part of the stream comprising ethylene and ethane as obtained in step (d) through a second membrane, preferably a membrane comprising metal cations, more preferably a membrane comprising comprising silver(I) ions ($Ag^+$ ions) or copper(I) ions ($Cu^+$ ions), to obtain a stream comprising ethane and ethylene and a stream comprising ethylene;

(hA) optionally feeding at least a part of the stream comprising ethane and ethylene as obtained in step (gA) to the membrane used in step (d), that is to say to the first membrane, or optionally feeding at least a part of the stream comprising ethane and ethylene as obtained in step (gA) to step (a).

Steps (eA) and (fA) are as described above. At least a part of the stream comprising ethane as obtained in step (eA) may be fed to step (a). Alternatively or additionally, at least a part of the stream comprising ethane as obtained in step (eA) may be converted to ethylene, for example by subjecting it to ethane cracking (pyrolysis) conditions.

Step (gA) is as described for step (g) above. Step (hA) is as described for step (h) above. Alternatively or additionally, step (hA) may comprise optionally converting ethane from the stream comprising ethane and ethylene as obtained in step (gA) to ethylene, for example by subjecting it to ethane cracking (pyrolysis) conditions as described above.

Membrane, PSA and Distillation

In one preferred embodiment of the process use is made of a membrane, a Pressure Swing Adsorption (PSA) unit and a distillation column. A schematic drawing of a preferred example of this embodiment is shown in FIG. 5, which is described in detail in the "Figures" section.

In this preferred embodiment, in step (d) a stream comprising ethane and methane and a stream comprising ethylene and ethane are obtained, and step (d) is followed by the following steps:

(eA) feeding the stream comprising ethane and methane as obtained in step (d) to a Pressure Swing Adsorption (PSA) unit to obtain a stream comprising ethane and a stream comprising methane;

(fA) optionally feeding at least a part of the stream comprising methane as obtained in step (eA) to step (a);

(gB) feeding the stream comprising ethylene and ethane as obtained in step (d) to a distillation column to obtain a stream comprising ethane and a stream comprising ethylene;

(hB) optionally feeding at least a part of the stream comprising ethane as obtained in step (gB) to step (a).

Steps (eA) and (fA) are as described above. At least a part of the stream comprising ethane as obtained in step (eA) may be fed to step (a). Alternatively or additionally, at least a part of the stream comprising ethane as obtained in step (eA) may be converted to ethylene, for example by subjecting it to ethane cracking (pyrolysis) conditions.

Preferably, before carrying out step (gB), any water is removed, as described above in relation to an optional distillation step preceding step (d). The distillation in step (gB) preferably is performed at a pressure in the range of from 1 to 100 bara, preferably 10 to 50 bara, more preferably 15 to 35 bara. Alternatively or additionally, step (fA) may comprise optionally feeding at least a part of the stream comprising ethane as obtained in step (eA) to distillation step (gB). Alternatively or additionally, step (hB) may comprise optionally converting ethane from the stream comprising ethane as obtained in step (gB) to ethylene, for example by subjecting it to ethane cracking (pyrolysis) conditions as described above.

Distillation, Membrane and PSA

In one preferred embodiment of the process use is made of a distillation column, a membrane and a Pressure Swing Adsorption (PSA) unit. A schematic drawing of a preferred example of this embodiment is shown in FIG. 6, which is described in detail in the "Figures" section.

In this preferred embodiment, at least a part of the gas stream comprising ethylene, ethane and methane as obtained in step (c) is subjected to distillation, resulting in a stream comprising methane and a stream comprising ethylene, ethane and methane which latter stream is fed to step (d), and step (d) is followed by the following steps:

(eA) feeding the stream comprising ethane and methane as obtained in step (d) to a Pressure Swing Adsorption (PSA) unit to obtain a stream comprising ethane and a stream comprising methane;

(fA) optionally feeding at least a part of the stream comprising methane as obtained in step (eA) to step (a);

(gC) optionally feeding at least a part of the stream comprising methane as obtained in the distillation to step (a).

Preferably, before carrying out said distillation, any water is removed, as described above. Said distillation step results in a top stream comprising methane and a bottom stream comprising ethylene, ethane and methane. Said bottom stream is fed to step (d).

Steps (eA) and (fA) are as described above. At least a part of the stream comprising ethane as obtained in step (eA) may be fed to step (a). Alternatively or additionally, at least a part of the stream comprising ethane as obtained in step (eA) may be converted to ethylene, for example by subjecting it to ethane cracking (pyrolysis) conditions.

PSA, Membrane and Another PSA (or Distillation) (1)

In one preferred embodiment of the process use is made of a first Pressure Swing Adsorption (PSA) unit (upstream of the membrane), a membrane and a second PSA unit (downstream of the membrane). A schematic drawing of a preferred example of this embodiment is shown in FIG. 7, which is described in detail in the "Figures" section.

In this preferred embodiment, at least a part of the gas stream comprising ethylene, ethane and methane as obtained in step (c) is fed to a first Pressure Swing Adsorption (PSA) unit, resulting in a stream comprising methane and a stream comprising ethylene, ethane and methane which latter stream is fed to step (d), and step (d) is followed by the following steps:

(eA) feeding the stream comprising ethane and methane as obtained in step (d) to a second PSA unit to obtain a stream comprising ethane and a stream comprising methane;

(fA) optionally feeding at least a part of the stream comprising methane as obtained in step (eA) to step (a);

(gC) optionally feeding at least a part of the stream comprising methane as obtained in the first PSA step to step (a).

Optionally, before carrying out said first PSA step, any water is removed, as described above.

Steps (eA) and (fA) are as described above. Optionally, said step (eA) may be replaced by a step which comprises subjecting the stream comprising ethane and methane as obtained in step (d) to distillation to obtain a stream comprising ethane and a stream comprising methane. At least a part of the stream comprising ethane as obtained in said second PSA step (eA) or in the latter alternative distillation step may be fed to step (a). Alternatively or additionally, at least a part of the stream comprising ethane as obtained in said second PSA step (eA) or in the latter alternative distillation step may be converted to ethylene, for example by subjecting it to ethane cracking (pyrolysis) conditions.

PSA, Membrane and Another PSA (or Distillation) (2), Including Recycle

In another preferred embodiment of the process use is made of two Pressure Swing Adsorption (PSA) units (upstream of the membrane), a membrane and a recycle from the membrane to the first PSA unit. A schematic drawing of a preferred example of this embodiment is shown in FIG. 8, which is described in detail in the "Figures" section.

In this preferred embodiment, at least a part of the gas stream comprising ethylene, ethane and methane as obtained in step (c) is fed to a first Pressure Swing Adsorption (PSA) unit, resulting in a stream comprising methane and ethane and a stream comprising ethylene and ethane which latter stream is fed to step (d) to obtain a stream comprising ethane and ethylene and a stream comprising ethylene; the stream comprising ethane and ethylene as obtained in step (d) is recycled to the first PSA unit; the stream comprising methane and ethane as obtained in the first PSA step is fed to a second PSA unit to obtain a stream comprising ethane and a stream comprising methane; at least a part of the stream comprising methane as obtained in the second PSA step is optionally fed to step (a).

Optionally, before carrying out said first PSA step, any water is removed, as described above. Optionally, said second PSA step may be replaced by a step which comprises subjecting the stream comprising ethane and methane as obtained in the first PSA step to distillation to obtain a stream comprising ethane and a stream comprising methane. At least a part of the stream comprising ethane as obtained in said second PSA step or in the latter alternative distillation step may be fed to step (a). Alternatively or additionally, at least a part of the stream comprising ethane as obtained in said second PSA step or in the latter alternative distillation step may be converted to ethylene, for example by subjecting it to ethane cracking (pyrolysis) conditions.

FIGURES

The present invention will be further elucidated with reference to the drawings.

FIG. 1 is a schematic drawing of a process for oxidative coupling of methane in accordance with one embodiment of the present invention. Gas comprising oxygen and methane is fed (1) to a reactor (2). In the reactor (2), which is an OCM reactor, oxygen and methane are contacted with a catalyst comprising a mixed metal oxide. The reactor effluent comprising ethylene, ethane, methane, carbon dioxide and water is fed (3) to a separator (5). The reactor effluent is cooled. A liquid stream (7) comprising water is separated from the gas stream. The remaining gas stream comprising ethylene, ethane, methane and carbon dioxide is fed (6) to carbon dioxide removal unit (8). A suitable carbon dioxide removal agent fed to said carbon dioxide removal unit (8) may be an aqueous solution of a base, for example sodium hydroxide or an amine. A gas stream comprising ethylene, ethane and methane is fed to membrane (9). Membrane (9) may be a membrane as described above. A stream comprising ethane and methane (10) is obtained. And a stream comprising ethylene (11) is obtained.

The following FIGS. 2 to 8 elucidate further embodiments of the embodiment of FIG. 1.

FIG. 2 is a schematic drawing of a part of a preferred process in which two membranes and a distillation column are used. The stream comprising ethane and methane (10) is fed to a distillation column (31). A stream comprising methane (32) is obtained which is optionally recycled to OCM reactor (2) (see FIG. 1). A stream comprising ethane (33) is obtained. The stream comprising ethylene (11) also comprises ethane and is fed to a second membrane (34). Second membrane (34) may be the same as first membrane (9). A stream comprising ethylene (35), which is a product stream, is obtained. A stream comprising ethane and ethylene (36) is recycled to the first membrane (9). Said stream comprising ethane and ethylene (36) may also be recycled to OCM reactor (2) (see FIG. 1).

FIG. 3 is a schematic drawing of a part of a preferred process in which one membrane and a PSA unit are used. The stream comprising ethane and methane (10) is fed to a PSA unit (41). A stream comprising methane (42) is obtained which is optionally recycled to OCM reactor (2) (see FIG. 1). And a stream comprising ethane (43) is obtained.

FIG. 4 is a schematic drawing of a part of a preferred embodiment in which two membranes and a PSA unit are used. The stream comprising ethane and methane (10) is fed to a PSA unit (41). A stream comprising methane (42) is obtained which is optionally recycled to OCM reactor (2) (see FIG. 1). And a stream comprising ethane (43) is obtained. The stream comprising ethylene (11) also comprises ethane and is fed to a second membrane (34). Second membrane (34) may be the same as first membrane (9). A stream comprising ethylene (35), which is a product stream, is obtained. A stream comprising ethane and ethylene (36) is recycled to the first membrane (9). Said stream comprising ethane and ethylene (36) may also be recycled to OCM reactor (2) (see FIG. 1).

FIG. 5 is a schematic drawing of a part of a preferred process in which one membrane, a PSA unit and a distillation column are used. The stream comprising ethane and methane (10) is fed to a PSA unit (41). A stream comprising methane (42) is obtained which is optionally recycled to OCM reactor (2) (see FIG. 1). And a stream comprising ethane (43) is obtained. The stream comprising ethylene (11) also comprises ethane and is fed to a distillation column (51). A bottom stream comprising ethane (53) and a top stream comprising ethylene (52) are obtained.

FIG. 6 is a schematic drawing of a part of a preferred process in which a distillation column, a membrane and a PSA unit are used. A gas stream comprising ethylene, ethane and methane (61) originating from carbon dioxide removal unit (8) is fed to a distillation column (62). A bottom stream comprising ethylene, ethane and methane and a top stream comprising methane are obtained. Said bottom stream is fed to membrane (9). The stream comprising ethane and methane (10) is fed to a PSA unit (41). A stream comprising methane (42) is obtained which is optionally recycled to OCM reactor (2) (see FIG. 1). And a stream comprising ethane (43) is obtained.

FIG. 7 is a schematic drawing of a part of a preferred process in which a first PSA unit, a membrane and a second PSA unit are used. A gas stream comprising ethylene, ethane and methane (61) originating from carbon dioxide removal unit (8) is fed to a first PSA unit (62). A stream comprising ethylene, ethane and methane (64) and a stream comprising methane (63) are obtained. Said stream (64) is fed to membrane (9). The stream comprising ethane and methane (10) is fed to a PSA unit (41). A stream comprising methane (42) is obtained which is optionally recycled to OCM reactor (2) (see FIG. 1). And a stream comprising ethane (43) is obtained.

FIG. 8 is a schematic drawing of a part of a preferred process in which first and second PSA units and a membrane are used. A gas stream comprising ethylene, ethane and methane (61) originating from carbon dioxide removal unit (8) is fed to a first PSA unit (62). A stream comprising ethylene and ethane (64) and a stream comprising methane and ethane (63) are obtained. Said stream (64) is fed to membrane (9) to obtain a stream comprising ethane and ethylene (10) and a stream comprising ethylene (11). The stream comprising ethane and ethylene (10) is recycled to the first PSA unit (62). Said stream comprising methane and ethane (63) is fed to a second PSA unit (41) to obtain a stream comprising methane (42) and a stream comprising ethane (43). Said stream comprising methane (42) is optionally recycled to OCM reactor (2) (see FIG. 1).

That which is claimed is:

1. A process for oxidative coupling of methane (OCM), comprising the steps of:
   (a) contacting, in a reactor, oxygen and methane with an OCM catalyst, resulting in a reactor effluent comprising ethylene, ethane, methane, carbon dioxide and water;
   (b) cooling the reactor effluent to obtain a liquid stream comprising water and a gas stream comprising ethylene, ethane, methane and carbon dioxide;
   (c) removing carbon dioxide from at least a part of the gas stream comprising ethylene, ethane, methane and carbon dioxide resulting in a gas stream comprising ethylene, ethane and methane;
   (d) passing at least a part of the gas stream comprising ethylene, ethane and methane as obtained in step (c) through a membrane to obtain a stream comprising ethane and methane and a stream comprising ethylene and ethane;
   (e) feeding the stream comprising ethane and methane as obtained in step (d) to a distillation column to obtain a stream comprising ethane and a stream comprising methane;
   (f) optionally feeding at least a part of the stream comprising methane as obtained in step (e) to step (a);
   (g) passing at least a part of the stream comprising ethylene and ethane as obtained in step (d) through a second membrane to obtain a stream comprising ethane and ethylene and a stream comprising ethylene; and
   (h) optionally feeding at least a part of the stream comprising ethane and ethylene as obtained in step (g) to the membrane used in step (d), or optionally feeding at least a part of the stream comprising ethane and ethylene as obtained in step (g) to step (a).

2. The process according to claim 1, wherein the membrane comprises metal cations.

3. The process according to claim 2, wherein the membrane comprises silver(I) ions (Ag+ions) or copper(I) ions ($Cu^+$ ions).

4. A process for oxidative coupling of methane (OCM), comprising the steps of:
   (a) contacting, in a reactor, oxygen and methane with an OCM catalyst, resulting in a reactor effluent comprising ethylene, ethane, methane, carbon dioxide and water;
   (b) cooling the reactor effluent to obtain a liquid stream comprising water and a gas stream comprising ethylene, ethane, methane and carbon dioxide;
   (c) removing carbon dioxide from at least a part of the gas stream comprising ethylene, ethane, methane and carbon dioxide resulting in a gas stream comprising ethylene, ethane and methane;
   (d) passing at least a part of the gas stream comprising ethylene, ethane and methane as obtained in step (c) through a membrane to obtain a stream comprising ethane and methane and a stream comprising ethylene and ethane;
   (eA) feeding the stream comprising ethane and methane as obtained in step (d) to a Pressure Swing Adsorption (PSA) unit to obtain a stream comprising ethane and a stream comprising methane; and
   (fA) optionally feeding at least a part of the stream comprising methane as obtained in step (eA) to step (a).

5. The process according to claim 4, wherein step (d) is followed by the following steps:
   (gA) passing at least a part of the stream comprising ethylene and ethane as obtained in step (d) through a second membrane to obtain a stream comprising ethane and ethylene and a stream comprising ethylene; and
   (hA) optionally feeding at least a part of the stream comprising ethane and ethylene as obtained in step (gA) to the membrane used in step (d), that is to say to the first membrane, or optionally feeding at least a part of the stream comprising ethane and ethylene as obtained in step (gA) to step (a).

6. The process according to claim 5, wherein the second membrane comprises metal cations.

7. The process according to claim 6, wherein the second membrane comprises silver(I) ions ($Ag^+$ ions) or copper(I) ions ($Cu^+$ ions).

8. The process according to claim 4, wherein step (d) is further followed by:
   (gB) feeding the stream comprising ethylene and ethane as obtained in step (d) to a distillation column to obtain a stream comprising ethane and a stream comprising ethylene; and
   (hB) optionally feeding at least a part of the stream comprising ethane as obtained in step (gB) to step (a).

9. A process for oxidative coupling of methane (OCM), comprising the steps of:
   (a) contacting, in a reactor, oxygen and methane with an OCM catalyst, resulting in a reactor effluent comprising ethylene, ethane, methane, carbon dioxide and water;
   (b) cooling the reactor effluent to obtain a liquid stream comprising water and a gas stream comprising ethylene, ethane, methane and carbon dioxide;
   (c) removing carbon dioxide from at least a part of the gas stream comprising ethylene, ethane, methane and carbon dioxide resulting in a gas stream comprising ethylene, ethane and methane, wherein at least a part of the gas stream comprising ethylene, ethane and methane is subjected to distillation, resulting in a stream comprising methane and a stream comprising ethylene, ethane and methane,
   (d) passing at least a part of the gas stream comprising ethylene, ethane and methane as obtained in step (c) through a membrane to obtain a stream comprising ethane and methane and a stream comprising ethylene and ethane;
   (eA) feeding the stream comprising ethane and methane as obtained in step (d) to a Pressure Swing Adsorption (PSA) unit to obtain a stream comprising ethane and a stream comprising methane;
   (fA) optionally feeding at least a part of the stream comprising methane as obtained in step (eA) to step (a); and
   (gC) optionally feeding at least a part of the stream comprising methane as obtained in the distillation to step (a).

10. A process for oxidative coupling of methane (OCM), comprising the steps of:

(a) contacting, in a reactor, oxygen and methane with an OCM catalyst, resulting in a reactor effluent comprising ethylene, ethane, methane, carbon dioxide and water;
(b) cooling the reactor effluent to obtain a liquid stream comprising water and a gas stream comprising ethylene, ethane, methane and carbon dioxide;
(c) removing carbon dioxide from at least a part of the gas stream comprising ethylene, ethane, methane and carbon dioxide resulting in a gas stream comprising ethylene, ethane and methane, wherein at least a part of the gas stream comprising ethylene, ethane and methane is fed to a first Pressure Swing Adsorption (PSA) unit, resulting in a stream comprising methane and a stream comprising ethylene, ethane and methane stream is fed to step (d);
(d) passing at least a part of the gas stream comprising ethylene, ethane and methane as obtained in step (c) through a membrane to obtain a stream comprising ethane and methane and a stream comprising ethylene and ethane;
(eA) feeding the stream comprising ethane and methane as obtained in step (d) to a second PSA unit to obtain a stream comprising ethane and a stream comprising methane;
(fA) optionally feeding at least a part of the stream comprising methane as obtained in step (eA) to step (a); and
(gC) optionally feeding at least a part of the stream comprising methane as obtained in the first PSA step to step (a).

11. A process for oxidative coupling of methane (OCM), comprising the steps of:

(a) contacting, in a reactor, oxygen and methane with an OCM catalyst, resulting in a reactor effluent comprising ethylene, ethane, methane, carbon dioxide and water;
(b) cooling the reactor effluent to obtain a liquid stream comprising water and a gas stream comprising ethylene, ethane, methane and carbon dioxide;
(c) removing carbon dioxide from at least a part of the gas stream comprising ethylene, ethane, methane and carbon dioxide resulting in a gas stream comprising ethylene, ethane and methane, wherein at least a part of the gas stream comprising ethylene, ethane and methane is fed to a first Pressure Swing Adsorption (PSA) unit, resulting in a stream comprising methane and ethane and a stream comprising ethylene, ethane and methane;
(d) passing at least a part of the gas stream comprising ethylene, ethane and methane as obtained in step (c) through a membrane to obtain a stream comprising ethane and ethylene and a stream comprising ethylene; the stream comprising ethane and ethylene as obtained in step (d) is recycled to the first PSA unit;
wherein the stream comprising methane and ethane as obtained in the first PSA step is fed to a second PSA unit to obtain a stream comprising ethane and a stream comprising methane; and at least a part of the stream comprising methane as obtained in the second PSA step is optionally fed to step (a).

12. The process according to claim 11, wherein the membrane comprises metal cations.

13. The process according to claim 12, wherein the membrane comprises silver(I) ions ($Ag^+$ ions) or copper(I) ions ($Cu^+$ ions).

* * * * *

UNITED STATES PATENT AND TRADEMARK OFFICE
CERTIFICATE OF CORRECTION

PATENT NO. : 11,117,848 B2
APPLICATION NO. : 16/500249
DATED : September 14, 2021
INVENTOR(S) : Georgios Mitkidis Page 1 of 1

It is certified that error appears in the above-identified patent and that said Letters Patent is hereby corrected as shown below:

In the Specification

Column 1, Line 61, delete "dessicant" and insert -- desiccant --, therefor.

Column 7, Line 58, delete "polysulphone," and insert -- polysulfone, --, therefor.

Column 9, Lines 61-62, delete "comprising comprising" and insert -- comprising --, therefor.

Column 11, Lines 6-7, delete "comprising comprising" and insert -- comprising --, therefor.

In the Claims

Column 15, Line 52, Claim 3, delete "(Ag+ions)" and insert -- ($Ag^+$ ions) --, therefor.

Column 16, Lines 18-19, Claim 5, after "(d)," delete "that is to say to the first membrane,".

Column 16, Line 50, Claim 9, delete "methane," and insert -- methane; --, therefor.

Column 16, Line 51, Claim 9, delete "(d)passing" and insert -- (d) passing --, therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*